(12) United States Patent
Kumakhov (10) Patent No.: US 7,110,503 B1
(45) Date of Patent: Sep. 19, 2006

(54) X-RAY MEASURING AND TESTING SYSTEM (76) Inventor: Muradin Abubekirovich Kumakhov, ul. Narodnogo Opolcheniya, d. 38, kv. 55, Moscow 123298 (RU)

( * ) Notice: Subject to any disclaimer, the term of this patent is extended or adjusted under 35 U.S.C. 154(b) by 0 days.

(21) Appl. No.: 10/181,561

(22) PCT Filed: Aug. 7, 2000

(86) PCT No.: PCT/RU00/00324

§ 371 (c)(1),
(2), (4) Date: Jul. 18, 2002

(87) PCT Pub. No.: WO02/12871

PCT Pub. Date: Feb. 14, 2002

(51) Int. Cl.
*H05J 35/00* (2006.01)
*H05G 2/00* (2006.01)
*G21K 1/06* (2006.01)

(52) U.S. Cl. .................. 378/119; 378/84; 378/85
(58) Field of Classification Search .......... 378/34, 378/70, 84, 119, 121, 143–147, 148, 149, 378/85, 124, 134; 250/505.1, 504 R; 315/503
See application file for complete search history.

(56) References Cited

U.S. PATENT DOCUMENTS

| | | | | |
|---|---|---|---|---|
| 3,980,568 A * | 9/1976 | Pitchford et al. | .............. | 378/46 |
| 4,280,049 A | 7/1981 | Werner | ................... | 250/310 |
| 4,631,743 A * | 12/1986 | Tomimasu et al. | .......... | 378/138 |
| 4,719,645 A * | 1/1988 | Yamabe et al. | ............. | 378/144 |
| 4,899,354 A * | 2/1990 | Reinhold | ................... | 378/34 |
| 5,001,734 A * | 3/1991 | Uda et al. | ................... | 378/34 |
| 5,031,199 A * | 7/1991 | Cole et al. | ................... | 378/34 |
| 5,073,913 A * | 12/1991 | Martin | ................... | 378/34 |
| 5,175,755 A * | 12/1992 | Kumakhov | ................... | 378/34 |
| 5,204,506 A * | 4/1993 | Asmus et al. | .......... | 219/121.37 |
| 5,394,451 A * | 2/1995 | Miyake et al. | ................ | 378/34 |
| 5,459,771 A * | 10/1995 | Richardson et al. | ........ | 378/119 |
| 5,497,008 A * | 3/1996 | Kumakhov | .............. | 250/505.1 |
| 5,512,759 A * | 4/1996 | Sweatt | ................... | 250/492.1 |
| 5,570,408 A * | 10/1996 | Gibson | ................... | 378/145 |
| 5,588,034 A | 12/1996 | Bowen | ................... | 378/73 |
| 5,623,529 A * | 4/1997 | Ebinuma et al. | .............. | 378/34 |
| 5,717,214 A * | 2/1998 | Kitamura et al. | ........ | 250/370.1 |
| 5,745,547 A * | 4/1998 | Xiao | ................... | 378/145 |
| 5,768,339 A * | 6/1998 | O'Hara | ................... | 378/147 |
| 5,784,430 A * | 7/1998 | Sredniawski | ................ | 378/57 |
| 5,812,631 A * | 9/1998 | Yan et al. | ................... | 378/85 |

(Continued)

FOREIGN PATENT DOCUMENTS

GB 2133208 7/1984

(Continued)

OTHER PUBLICATIONS

Shu et al., Rev. Sci. Instrum. 66 (2), 1795-1797 (1995).*

(Continued)

*Primary Examiner*—Allen C. Ho
(74) *Attorney, Agent, or Firm*—McDermott Will & Emery LLP (57) ABSTRACT

The complex is intended for carrying out research in the X-ray range at several analytical devices 5 simultaneously. The complex comprises a source 1 of divergent X-rays, for example an X-ray tube and x-ray lenses 2 for radiation transporting toward the analytical devices 5 and the apparatus of these devices. The X-ray lenses 2 form the x-rays into quasi-parallel beams. Usage of the X-ray lenses provides for the scientists in the analytical devices the requisite brightness, being not less than in the complexes where the radiation source is a synchrotron.

15 Claims, 7 Drawing Sheets

U.S. PATENT DOCUMENTS

| | | | |
|---|---|---|---|
| 6,041,098 A * | 3/2000 | Touryanski et al. | 378/70 |
| 6,049,588 A * | 4/2000 | Cash, Jr. | 378/85 |
| 6,069,937 A * | 5/2000 | Oshino et al. | 378/119 |
| 6,072,853 A * | 6/2000 | Hall | 378/73 |
| 6,226,347 B1 * | 5/2001 | Golenhofen | 378/45 |
| 6,324,255 B1 * | 11/2001 | Kondo et al. | 378/119 |
| 6,487,272 B1 * | 11/2002 | Kutsuzawa | 378/140 |
| 6,678,348 B1 * | 1/2004 | Kumakhov | 378/84 |
| 6,754,302 B1 * | 6/2004 | Kitaoka | 378/34 |
| 6,754,304 B1 * | 6/2004 | Kumakhov | 378/45 |
| 6,949,748 B1 * | 9/2005 | Ziock et al. | 250/370.01 |

FOREIGN PATENT DOCUMENTS

| | | |
|---|---|---|
| RU | 2112290 | 5/1998 |
| RU | 2115943 | 7/1998 |
| RU | 2129698 | 4/1999 |
| RU | 2161843 | 1/2001 |
| WO | 96/29723 | 9/1996 |

OTHER PUBLICATIONS

Thiel et al., Rev. Sci. Instrum. 64 (10), 2872-2878 (1993).*

Sinkhrotronnoe izluchenie. Svoista I primenenie. Under editorship K Kuntsa. Moscow, Mir. 1981, pp. 76-77, pp. 80-83. (Labeled "Document A").

F.N. Kharadzha. Obschy kurs rentgenotekhniki Izdanie tretie. Moscow-Leningrad, izd "energiya", 1966, pp. 74, 75, 78, 81, 84. (Labeled "Document B").

Fizicheskaya entsiklopediya. Chief Editor A M Prokhoro. vol. 4. Moscow, "Bolshaya Rossiiskaya entsiklopediya", 1994, pp. 365-366. pp. 344-345 (Labeled "Document C").

* cited by examiner

X-RAY MEASURING AND TESTING SYSTEM

FIELD OF THE INVENTION

The invention relates to the technique of researching and testing substances, materials or devices with the use of X-rays.

BACKGROUND ART

The complexes for carrying out the mentioned researches and simultaneously testing on several analytical devices are known (see: Synchrotron Radiation. Ed. by K. Kunts. Moscow, "Mir", 1981, pp. 80–89 [1]). A radiation source, common for all analytical devices, is used in such complexes. The said source represents a synchrotron, or a storage ring in more modern complexes. The synchrotron radiation, emerging from the synchrotron or the storage ring, is transported to the analytical devices (work stations). A spectral band, needed for carrying out the particular researches or tests, is extracted from the quite broadband synchrotron radiation (in the case, the suggested invention is related to, this band is in the X-ray range). The components of the apparatus of each analytical device is defined by its specialization in one or another type of researches and tests.

However, it is known, that the synchrotron radiation sources, including the storage rings, represent very complicated major constructions, which cost reaches hundreds of millions of dollars. So, the storage rings, which radiation spectrum includes the X-ray range, are of not less than 50 m diameter ([1], p. 80).

When the said synchrotron radiation sources are in use, taking into account the huge sizes of the said constructions, the most complicated problem is the maintenance of the tolerable vacuum level, both in the synchrotron radiation transporting channels (open to the accumulator) to the analytical devices, distanced from the ring periphery on tens meters, and in the experimental volume of each analytical device. The vacuum deterioration in any analytical device can put out of action the device not only in the accumulator itself, but as well in all devices, connected with it ([1], p. 80).

The X-rays extracting and forming some beams according to the number of the analytical devices from the narrow directed beam emerging from the synchrotron or the storage ring, which must be realized in the vacuum, represent a serious task, which can be solved by means of the system of the grazing mirrors and the crystals. When using the channels of the mentioned extent, the special steps should be taken to ensure the control and maintenance of the position of each formed beam, which width in a vertical plane is unities of mrad. So, if at the distance of 40 m the beam is displaced no more than at 10 mm, one or two orders of the intensity are lost, depending on the aperture of the analytical device ([1], p. 85).

For the synchrotrons and the storage rings of the said sizes it is difficult as well to solve the problem of the radiation shielding of both the staff, working with a synchrotron or an accelerator, and the research staff of the analytical devices.

At least, the complexes on the basis of the synchrotrons or the storage rings are so expensive, that only few governments can finance their building. Therefore there are only very few of them, and for the last decades the governments must unite to build such complexes. The European center of synchrotron radiation is an example of such complexes (Grenoble, France).

In spite of the noted disadvantages the sources of a synchrotron radiation, nowadays they are practically unique type of the sources, making possible to obtain a spectral plane of the narrow directed radiation, being enough for the research and test aims, in the required working range simultaneously for some analytical devices.

Therefore it is very important to create a complex, available for scientists and engineers, where a high brightness of a radiation on the input aperture of the analytical devices at the usage of the cheap sources can be obtained.

The suggested invention provides the creation of a complex, being free of the said disadvantages (huge sizes, very high price, the problems of the vacuum maintenance, providing the radiation safety, some beams forming and controlling when a radiation is transported to the analytical devices).

SUMMARY OF THE INVENTION

The suggested measuring and testing complex for researches in the X-ray range on several analytical devices simultaneously, as well as the known one, comprises a radiation source, channels of radiation transporting to the analytical devices and apparatus of the analytical devices.

As distinct from the known one, the suggested complex contains a divergent X-ray source as a radiation source, each channel of radiation transporting to the analytical devices comprises an X-ray lens made as a package of curved channels with the use of multiple total external reflection of X-rays from their walls, the said lens is placed with a capability of capturing a part of the divergent X-rays of the source and with a capability of transforming the said X-rays to a quasi-parallel one. An X-ray tube, laser or plasma source can be used as a source of the divergent X-rays.

Thus the said types of the technical results is provided by the suggested invention owing to the refusal from a synchrotron or a storage ring as a radiation source and the usage, in particular, of a standard X-ray tube as the said source, and X-ray lenses for radiation extracting and forming the narrow directed quasi-parallel beams, which transport X-rays to the analytical devices.

Besides, the complex can comprise in addition an X-ray lens as a package of curved channels with the use of multiple total external reflection of X-rays from their walls, and the said lens is located with a capability of capturing a part of divergent X-rays of the source and the said lens is made with a capability of transforming the said X-rays, as well as an analytical device made with a capability of an object under study placing together with aligning the required part of the said object with an area of X-rays focusing.

When a divergent X-rays of an X-ray tube is used as a source in the suggested complex, the said tube can be made with different types of an anode, in particular, it can be microfocal, through, rotating, complex, tungsten. It is worthwhile to use an X-ray tube with a microfocal or through anode in order to produce the radiation, diverging in a wide solid angle; a tube with a complex anode to provide a possibility of obtaining different spectral lines of a radiation with respect to chemical elements, being a part of the anode; a tube with a rotating anode to provide a capability of obtaining more density owing to the improvement of heat removal; a tube with a tungsten anode for a broadband X-rays producing.

In cases when the suggested complex includes a tube with a rotating, complex or tungsten anode as a divergent X-ray source, the said complex can comprise in addition at least one monochromator, placed on a path of a quasi-parallel beam, formed by an X-ray lens, with a capability of extracting and reflecting a part of this beam toward the analytical device. In such cases a quasi-parallel beam, formed by one X-ray lens, is used to provide X-rays for at least two analytical devices.

In a case when an analytical device, being a part of the suggested complex, is intended for carrying out spectrometric researches, it includes a means for placing a sample under study, a detector of the radiation, excited in the sample, a spectrometric channel, connected up to the output of the detector, and a means of data processing and imaging, connected up to the output of the spectrometric channel. Such an analytical device is placed on the part of the output focus region of the X-ray lens, being a part of the complex, and the said lens is placed with a capability of capturing a part of a divergent X-rays of the source and the said lens is made with a capability of focusing the said radiation. This analytical device must be made with a capability of aligning the required part of the sample under study with the focus region of the said lens.

Analytical devices, a quasi-parallel beam of the radiation is transported to, have, in particular, the following possibilities.

If such analytical device is intended for carrying out the spectrometric researches, it comprises an X-ray lens in the form of a package of the curved channels with the use of multiple total external reflection of an X-rays from their walls, the said lens is placed and made with a capability of focusing a quasi-parallel beam of the radiation. The said analytical device comprises, as well, a means for placing the sample under study with aligning the required part of it with the focus region of the X-rays. Besides, the given analytical device comprises the detector of the radiation, excited in the sample under study, a spectrometric channel, connected up to the output of the detector, and a means of data processing and imaging, connected up to the output of the spectrometric channel.

In a case, when the analytical device, being a part of the suggested complex and a quasi-parallel beam of a radiation is transported to, is intended for carrying out diffractometric researches, the said analytical device comprises a means for placing and orienting the sample under study with respect to the direction of the beam propagation, a radiation detector diffracted on the sample under study, and a means for relative positioning the detector and the sample under study, and a means of the data processing and imaging connected up to the output of the detector.

In a case, when an analytical device, being a part of the suggested complex and a quasi-parallel beam of a radiation is transported to, is intended for image forming of the internal structure of the objects, the said analytical device comprises a means for the object positioning and a detector of the radiation, passed through the object, with the means of the image visualizing and registering.

In a case, when an analytical device, being a part of the suggested complex and a quasi-parallel beam of a radiation is transported to, is intended for carrying out X-ray lithography, the said analytical device comprises a means for placing a mask, and a means for placing a substrate with a layer of a resist, applied on its surface, thus the said means for placing a substrate is placed behind the said means for placing a mask.

BRIEF DESCRIPTION OF THE DRAWINGS

The suggested invention is illustrated with the drawings, which depict.

VARIANTS OF CARRYING OUT THE INVENTION

The suggested complex (FIG. 1) includes an X-ray tube 1, being a common X-ray source for the analytical devices (work stations) 5, each has a composition of apparatus, corresponding to the specialization of the analytical device on the definite type of researches, measurements or tests. Some X-ray lenses 2 (according to the number of the analytical devices 5) are placed in the solid angle, which corresponds to the radiation, being formed by the X-ray tube 1. Each of the said lenses captures a part of the radiation of the X-ray tube 1 in the solid angle 3 and transforms the divergent radiation, absorbed by it, to the beam 4 of the quasi-parallel radiation. The focus regions of the X-ray lenses 2 from the part of their input faces are aligned with each other and with the center of the output aperture of the X-ray tube 1, wherever possible.

Figure 1:
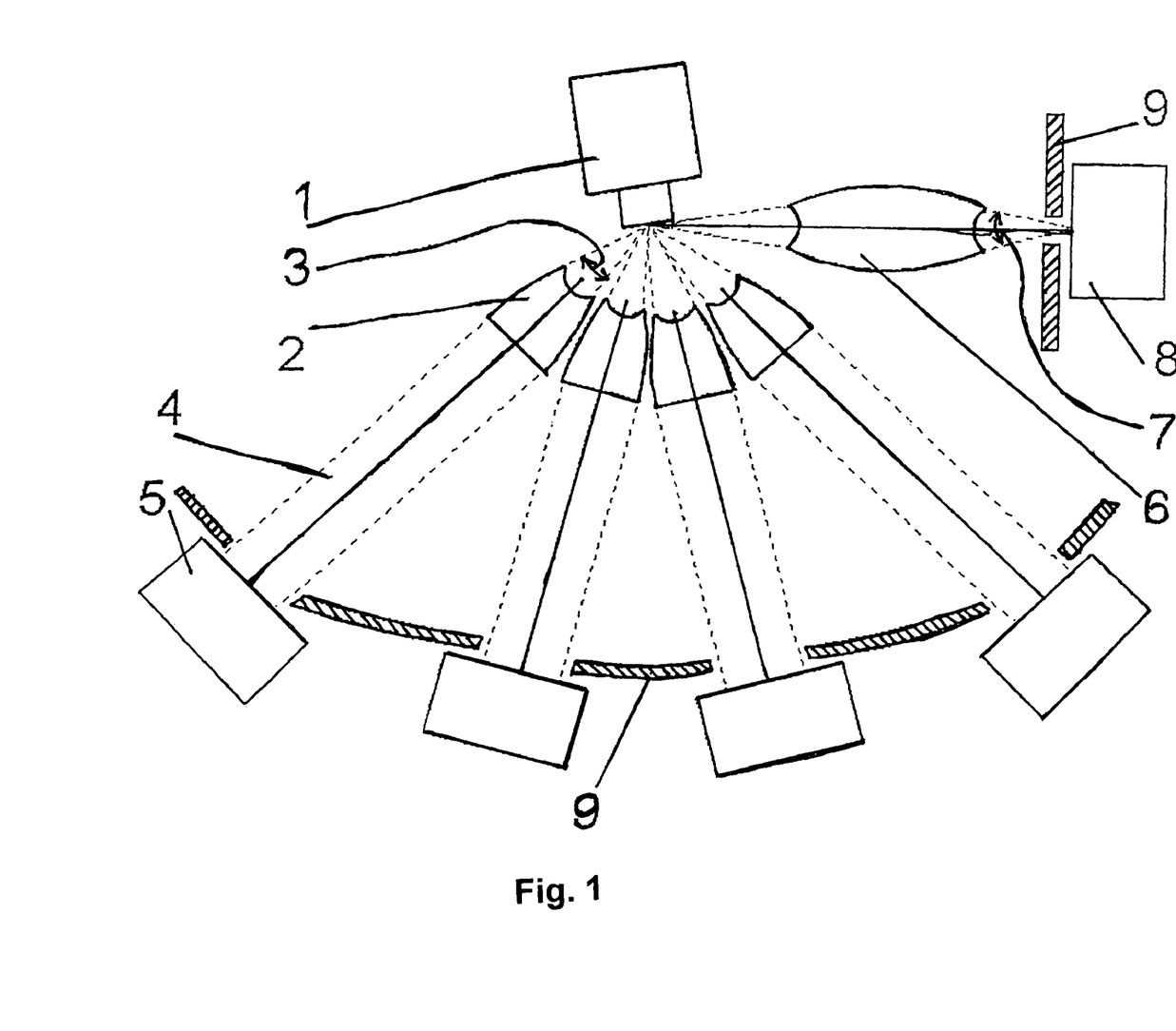
FIG. 1 depicts a composition and relative placement of the main parts of the suggested complex.

The output beam 2 of each of the lenses 2 is directed to the input aperture of the corresponding analytical device 5. The analytical devices 5 are placed from the X-ray lenses 2 at a distance, being chosen from accessibility considerations (the distance between the beams in the zone of the analytical devices placement must be enough for the apparatus and staff placing).

The X-ray lenses 2, made with a capability of transforming a divergent X-rays to a quasi-parallel one, together with the quasi-parallel beams 4, formed by the said lenses, form channels of X-rays transporting from the source (X-ray tube 1) to the analytical devices (work stations) 5.

In a specific case the complex can include, as well, one or more X-ray lenses 6, focusing the divergent radiation of the X-ray tube, absorbed by them, on the small area, being in the predetermined place on the input of the specialized analytical device 8, which demands precisely the character of the X-rays, acting on the object under study. The solid angle 7 corresponds to the focused output beam of the X-rays of the lens 6 in the FIG. 1. When needed the action, equivalent to the mentioned above, can be obtained in the complex, which does not include the focusing lenses 6 in the immediate radiation region of the X-ray tube, by way of the incorporation of the lens 5, analogous to one of the lenses 2 but being oriented oppositely to it, into the analytical device 5. Such lens transforms the X-ray quasi-parallel beam 4 to a focused one.

The protection of the staff of the analytical devices against the direct X-rays of the tube 1 is provided by the screen 9, having holes to size of the sections of the beams 4, 7. The protective screen 9 can be placed close to the analytical devices 5, 8 (FIG. 1 depicts this case), as well as close to the output faces of the X-ray lenses 2, 6. As the length of the beams 4 can be some meters and more, the sizes of the screen 9 in the first case are considerably more than in the second one. However it should be expected more action of errors of the protection screen production on the probability of the direct radiation acting of the X-ray tube 1 on the staff.

The most important components of the suggested complex are the X-ray lenses, owing to their usage it is possible to provide obtaining the technical results, which components were listed above in the summary of the invention.

Figure 2:
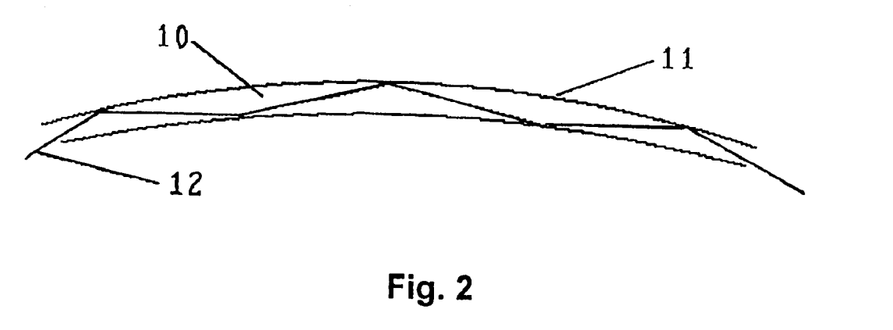
FIG. 2 depicts an X-rays propagation with multiple total external reflection along a separate channel of the X-ray lens.

The first lenses for X-rays controlling (focusing a divergent radiation, forming a parallel flux from the divergent radiation, focusing a parallel radiation, etc.) represented a package of curved, as required, channels 10 (FIG. 2) of the radiation transporting, where the radiation suffers the multiple total external reflection from the walls 11. The polygonal line 12 in the FIG. 2 shows the process of the multiple total external reflection of a separate quantum of X-rays when being propagated along of the channels 10 of the X-ray lens. Such lenses were made as a set of capillaries or polycapillaries, passing through the holes or cells of the supporting structures, placed on the definite distance along the lens length (see: V. A. Arkadiev, A. I. Kolomiitsev, M. A. Kumakhov, et al. Broadband X-ray optics with wide angle aperture. Uspekhi Phisicheskikh nauk, 1989, volume 157, issue 3, pp. 529–537 [2]; U.S. Pat. No. 5,192,869 (published Mar. 9, 1993) [3]). A lens as a whole is barrel shaped (i.e. it narrows toward the both faces), if it is intended for the divergent radiation focusing, or it is half-barrel shaped (i.e. it narrows only toward one of the faces), if it is intended for the divergent radiation transforming to a quasi-parallel one or for the such radiation focusing.

Thereafter the terms correspondingly a "full" lens and a "half" lens receive acceptance for designating the lenses of two said types, including the lenses which differ from the described ones in constructional embodiment. The appropriate nomenclature is used below when the suggested invention is described.

Figure 3:
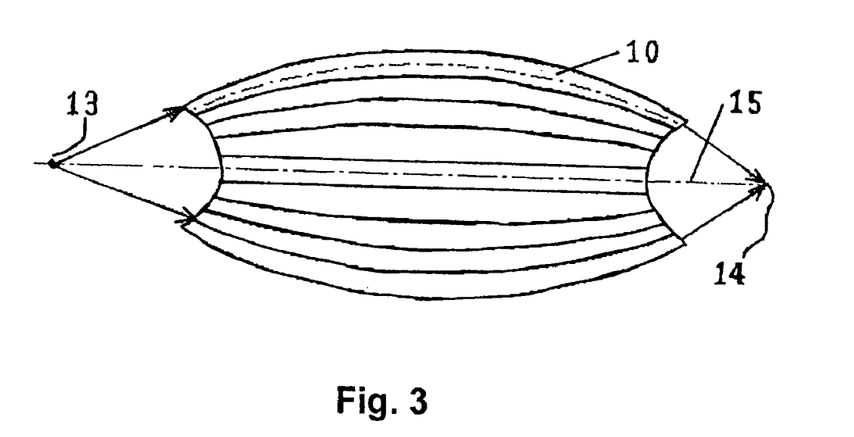
FIG. 3 depicts a diagram of an X-ray lens for a divergent radiation focusing (a "full" lens)

A lens is known, in which the walls of the neighboring radiation transporting channels contact each other along their full length, and the channels themselves have a cross-section, variable along its length and changing according the same law as a total cross-section of the lens (V. M. Andreevsky, M. V. Gubarev, P. I. Zhidkin, M. A. Kumakhov, A. V. Niskin, I. Yu. Ponomarev, Kh. Z. Ustok. X-ray waveguide system with a variable cross-section of the sections. The IV-th All-Union Conference on Interaction of Radiation with Solids. Book of Abstracts (May 15–9, 1990, Elbrus settlement, Kabardino-Balkarian ASSR, USSR, pp. 177–178 [4]; U.S. Pat. No. 5,570,408 (published Oct. 29, 1996) [5]). A "full" lens and a "half" lens with such channels are shown diagrammatically in FIG. 3 and FIG. 4 correspondingly.

A "full" lens (FIG. 3) has channels, curved so that their left and right continuations from the corresponding faces converge in the left 13 and right 14 focus regions, which size is a diameter of a separate channel order. The channels, placed closer to the periphery of the "full" lens, are curved more than the channels, placed closer to the lens optical axis 15, coinciding with the longitudinal axis of symmetry. To focus a divergent X-rays a quasi-point source must be in one of the focus regions, then focusing is realized in the other focus region.

Figure 4:
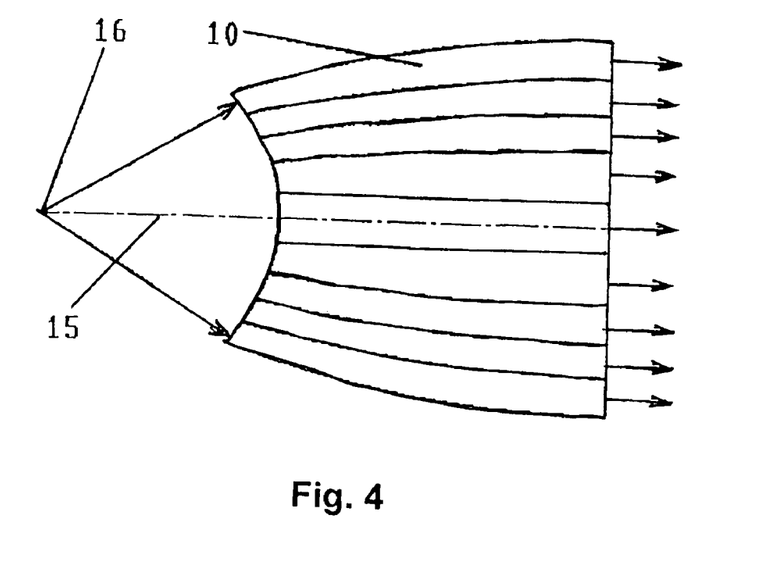
FIG. 4 depicts a diagram of an X-ray lens for a divergent radiation transforming to a quasi-parallel one (a "half" lens)

When a divergent radiation falls on the "half" lens, shown in FIG. 4, from the left, the said lens transforms it to a quasi-parallel radiation, emerging from the right face. The curvature of the channels, being various on the different distance from the optical axis 15 of the "half" lens, provides crossing of the continuations of their left ends in the focus region 16 of the "half" lens, thus the focus region 16 must coincide with the placement of the quasi-point source of the divergent X-rays; and the channels of the "half" lens are parallel to each other at the output face (the right one in FIG. 4). When a quasi-parallel X-rays falls on the right face of the "half" lens, according to FIG. 4, the said radiation is focused on the focus region 16, placed at the left face.

Owing to the usage of a source (an X-ray tube), forming direct X-rays, it is no need to use any means for extracting the radiation of X-ray range from the radiation of the source in the described complex. The extraction of the radiation and its distribution over the channels of transporting toward the analytical devices does not require any special means or techniques as well. It is sufficient to place the lenses 2, 6 in the zone of radiation exiting from the tube 1 at the distance, providing the vicinity of the focus regions of the lenses to the effective geometric center of the radiation of the tube 1.

It is no need to use any special means for maintenance the required trajectory of the formed rays (X-ray beams 4, 7) on the way to the analytical devices 5, 8 as well. It is sufficient to provide the relative mechanical immobility of the X-ray tube 1 and the lenses 2, 6. The features of the X-ray tube 1 and the X-ray lenses 2, 6 are stable and make it possible to do without any adjustments after the first proper installation.

As the beam length of the quasi-parallel radiation being transported, i.e. the distance between the output faces of the X-ray lenses and the analytical devices, does not exceed some meters (this distance is sufficient for convenient placement of the apparatus of the analytical device and for the staff), the X-rays damping and divergence are insignificant. Therefore the radiation transporting is possible directly in the air medium without taking any efforts for evacuation. Owing to this fact there are no problems with vacuum maintenance in the suggested complex.

The radiation protection, realized by means of the screen 9, is very simple constructively and can be provided by usual structural constructions at the low-power X-ray tube 1 (it will be shown below that it can be quite acceptable).

As against a synchrotron, which is characterized with the pulsed character of radiation, which parameters can not be changed by the staff of the analytical devices, an X-ray tube radiation may be both continuous and pulsed one with the desired parameters of the last one. Owing to the possibility of work at the continuous radiation, the researches can by carried out in the suggested complex, for which the pulsed radiation is unacceptable (for instance, because of the mean intensity of the pulsed radiation, being equal to the continuous radiation, the relations of nonlinear effects in the medium under study, caused by the high intensity in the pulse, are possible).

The analytical devices, being a part of the suggested complex, can be intended for solving a great number of different fundamental and applied tasks, for example, diffractometry and topography of simple, complex and protein crystals, the X-ray fluorescence analysis by means of focused X-ray beams, the image formation of the internal structure of different object, including biological in medical applications, the analysis of new materials and medicinal, the analysis of chips, features and quality of surfaces, etc.

Figure 5:
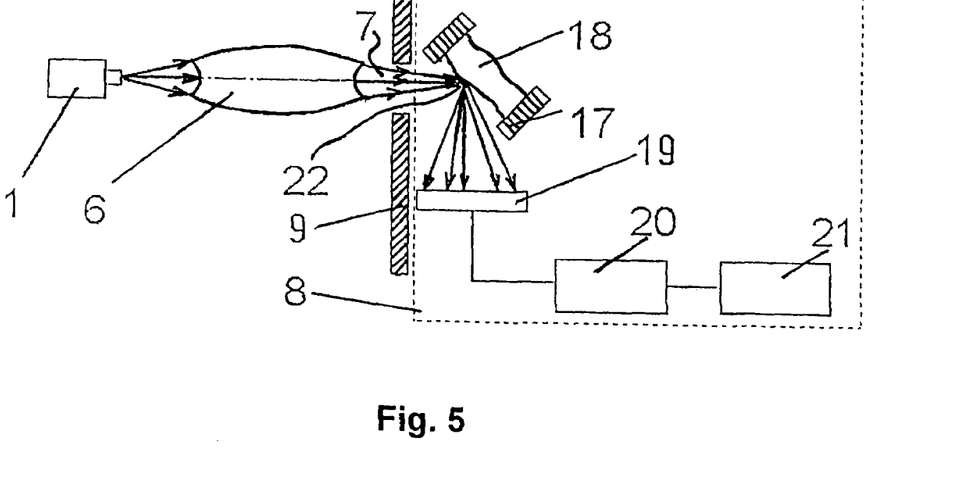
FIG. 5 depicts a composition and relative placement of apparatus of the analytical device, intended for carrying out spectrometric researches, in a case when the radiation of the source is transported to the said device by the "full" X-ray lens, which focuses the divergent radiation of the source.

In a case if an analytical device, being a part of the suggested complex, is intended for carrying out spectrometric researches, it comprises (FIG. 5) a means 17 for placing a sample under study 18, a detector 19 of the radiation excited in the sample, a spectrometric channel 20 connected up to the output of the detector 19, and a means 21 for data processing and imaging connected up to the output of the spectrometric channel 20. Such an analytical device 8 is placed on the part of the output focus region 22 of the "full" X-ray lens 6, being a part of the complex (see as well FIG. 1), and the said lens is placed with a capability of capturing a part of the divergent X-rays of the source 1 and made with a capability of focusing the said radiation. The means 17 for placing the sample under study must provide a possibility of aligning the required part of the sample under study 18 with the output focus region 22 (a right one in FIG. 1, FIG. 5) of the "full" lens 6. The information about the members of the spectrometric channel (an amplifier, a rejector of superpositions, a multichannel amplitude analyzer, and others), as well as about the means 21 of data processing and imaging are given, in particular, in the book: R. Volsdet. Applied spectrometry of X-rays. Moscow, Atomizdat, 1977 [6], chapter 2. A main field of application of the spectrometric researches is the determination of the elemental composition of the sample with the assessment of quantitative content of different chemical elements in the said sample.

Figure 6:
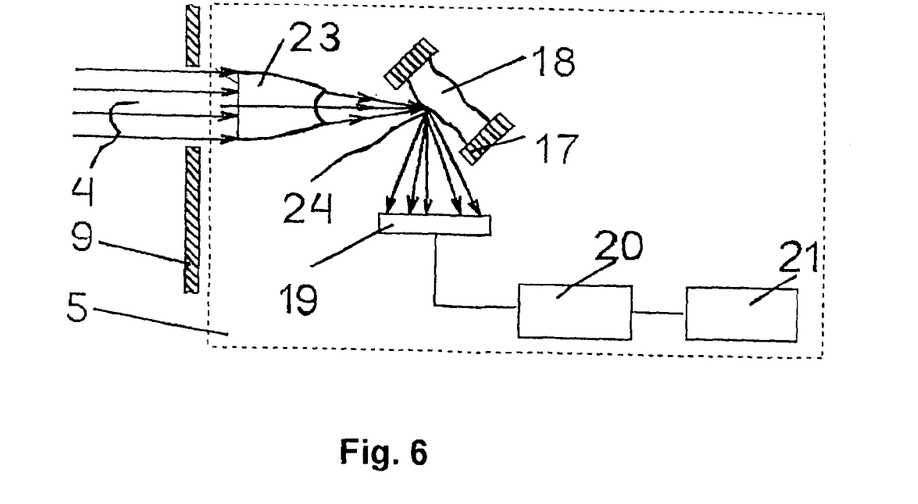
FIG. 6 depicts the same in a case, when a quasi-parallel radiation, formed by a "half" lens, is transported to the analytical device.

An analytical device, analogous to the described one, can use a quasi-parallel X-rays, as well, which beam is formed by one of the "half" lenses 2 (FIG. 1). It is enough for this purpose to complete the device 8, shown in FIG. 5, with the "half" lens 23 (see FIG. 6, where the device 5 with such and addition is shown). The focus region 24 of the "half" lens 23 plays a role of the output focus region of the "full" lens.

Figure 7:
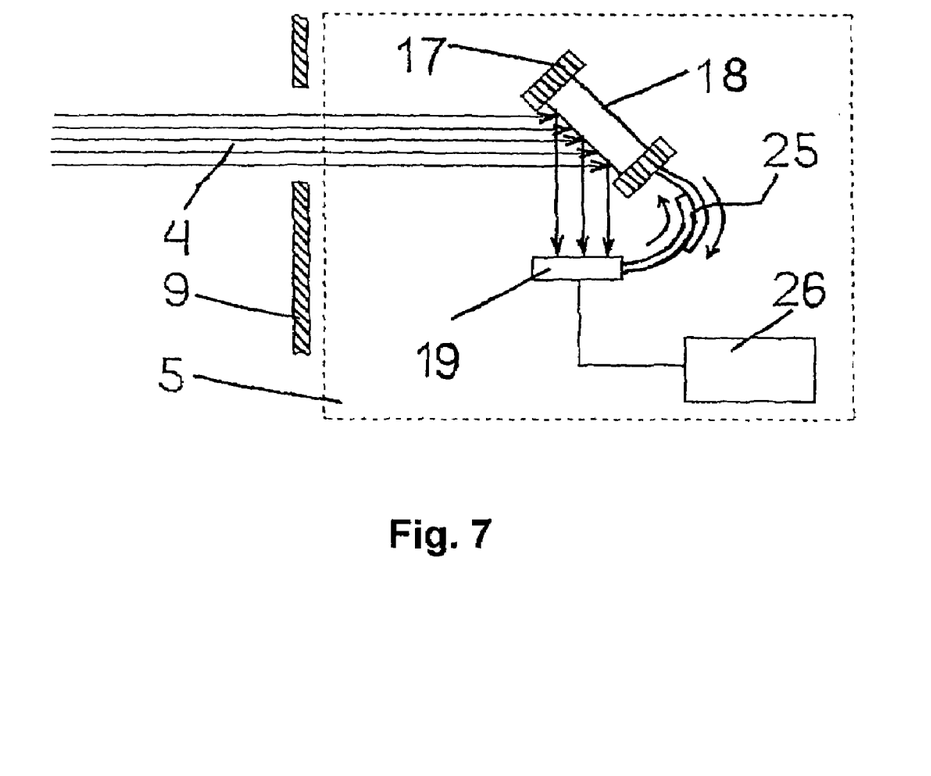
FIG. 7 depicts a composition and relative placement of apparatus of the analytical device, a quasi-parallel radiation is transported to, and the said analytical device is intended for carrying out diffractometric researches.

In a case, if an analytical device 5, being a part of the suggested complex and a quasi-parallel beam is transported to, is intended for carrying out the diffractometric researches, it comprises (FIG. 7) the means 17 for the sample under study 18 placing and its orienting relatively the direction of the beam 4 propagation, the detector 19 of the radiation, diffracted on the sample under study, and the means 25 for relative positioning the detector 19 and the sample under study 18, as well as the means 26 for data processing and imaging connected up to the output of the detector 19. The means 25 for relative positioning the detector and the sample under study and the means 17 for placing the sample under study and its orienting relatively the direction of the beam 4 propagation should provide the high angular accuracy, and the said means are made as goniometric mechanisms. The main field of application of such an analytical device is the research of the crystal samples.

Figure 8:
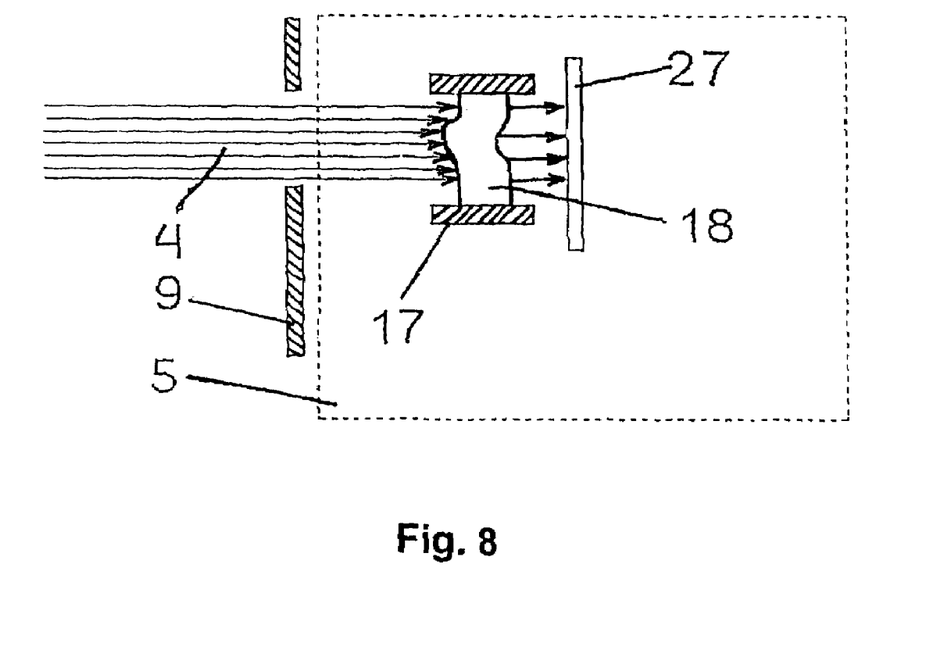
FIG. 8 depicts a composition and relative placement of apparatus of the analytical device, a quasi-parallel radiation is transported to, and the said analytical device is intended for image forming of the internal structure of the object.

In a case if the analytical device 5, being a part of the suggested complex and a quasi-parallel beam is transported to, is intended for the image formation of the internal structure of the objects, the said device comprises (FIG. 8) the means 17 for the object 18 positioning and the detector 27 of the radiation, passed through the object. In the simplest case a usual X-ray film in a packaging, protecting the film from the light action, is used as the said detector. The said film is functioning simultaneously as a means of image registering and a means of image visualizing, after it is developed. The other diagrams of image formation, applied in the analytical devices of the suggested complex, are described, for example, in the European application No. EP 0 742 150 (published Jul. 31, 1996) [7].

Figure 9:
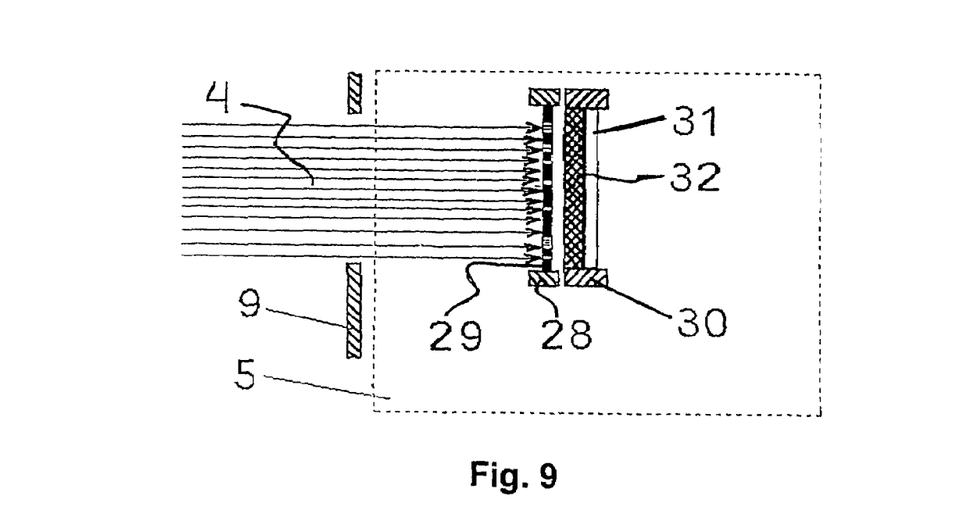
FIG. 9 depicts a composition and relative placement of apparatus of the analytical device, a quasi-parallel radiation is transported to, and the said analytical device is intended for carrying out X-ray lithography.

In a case, if the analytical device 5, being a part of the suggested complex and a quasi-parallel beam is transported to, is intended for realizing the X-ray lithography, the said device comprises (FIG. 9) the means 28 for the mask 29 positioning and the means 30 for the substrate 31 placing with a layer of the resist 32 applied on the said substrate, and the said means 30 is placed behind the said means 28. More complicated diagrams see, for example, in the U.S. Pat. No. 5,175,755 (published Dec. 29, 1992), [8].

A number of other examples of the structure of the analytical devices, including the usage of X-ray "full" and "half" lenses in them, is described, for instance, in U.S. Pat. No. 5,497,008 (published Mar. 5, 1996) [9] and in European patent No. EP 0 555 376 (published Mar. 18, 1998) [10].

If an anode of the tube is made of tungsten, it is possible to extract various wavelengths by means of monochromators, as the tungsten radiation is rather broadband and intensive.

If a complex target, made of some chemical elements, is used as an anode, so monochromators will extract selectively one or other wavelengths of characteristic radiations of the complex anode.

The choice of the type of the source of the divergent X-rays, being in usage, is defined, in particular, by the task to be solved. So, the radiation of laser and plasma sources of soft X-ray band can be used when the researches in biology, medicine are carried out, for microscopy, and others. Besides such sources, as well as the X-ray tubes of the sufficient power, can be used in the complexes, including the analytical devices (work stations), the tasks of the X-ray lithography (both contact and projection) and LIGA-technology are solved by means of.

The use of variable "geometry" of placing the anode of the tube, the X-ray lens and the analytical device depends on a type of an X-ray tube.

The geometry, described above and shown in FIG. 1, when each analytical device corresponds the X-ray lens, forming a radiation beam only for this analytical device, is one of possible as well. In this "geometry" it is appropriate to use, for example, the tubes with a through or microfocal anode. Such tubes practically radiate in the half-space, therefore major number of the "half" and "full" lenses can be placed in the solid angle of the said tube radiation.

Figure 10:
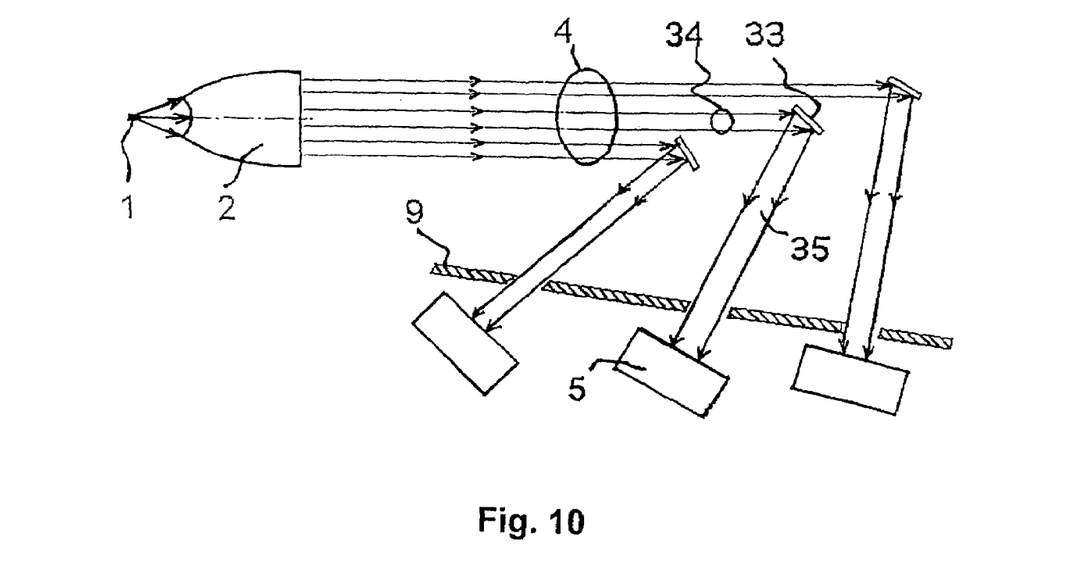
FIG. 10 depicts a variant of "the geometry" of placing the components of the suggested complex when using monochromators for a quasi-parallel beam splitting into parts, being transported to some analytical devices.
Figure 11:
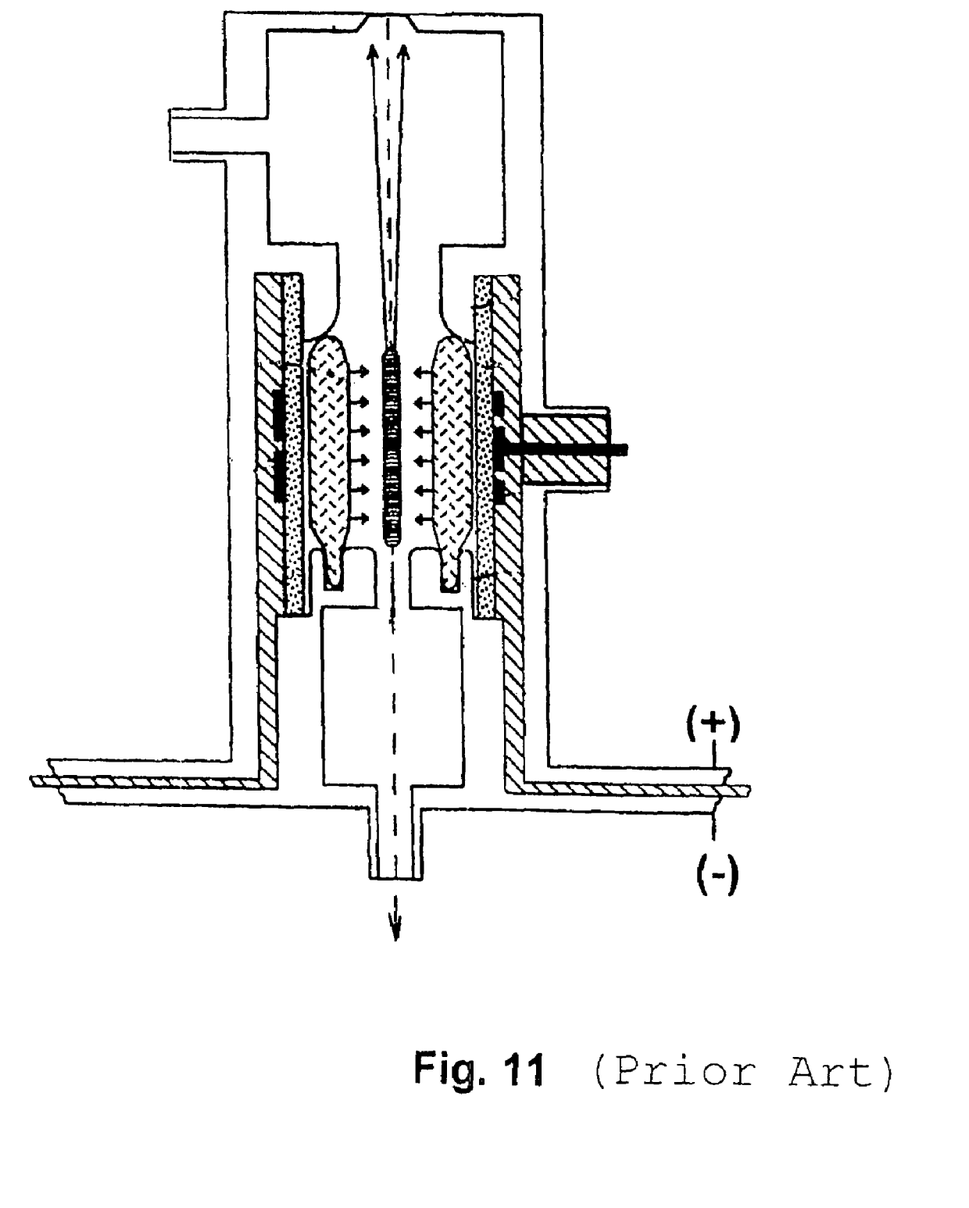
FIGS. 11 and 12 illustrate Prior Art structures of plasma and laser X-ray sources as known from U.S. Pat. No. 5,504,795 (McGeoch) and U.S. Pat. No. 6,333,966 (Kumakhov).
Figure 12:
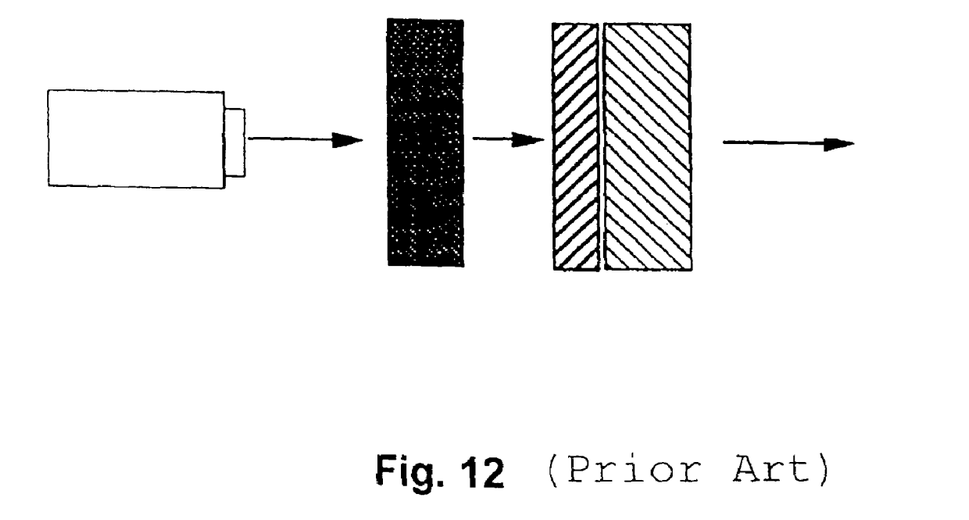
Figure 13:
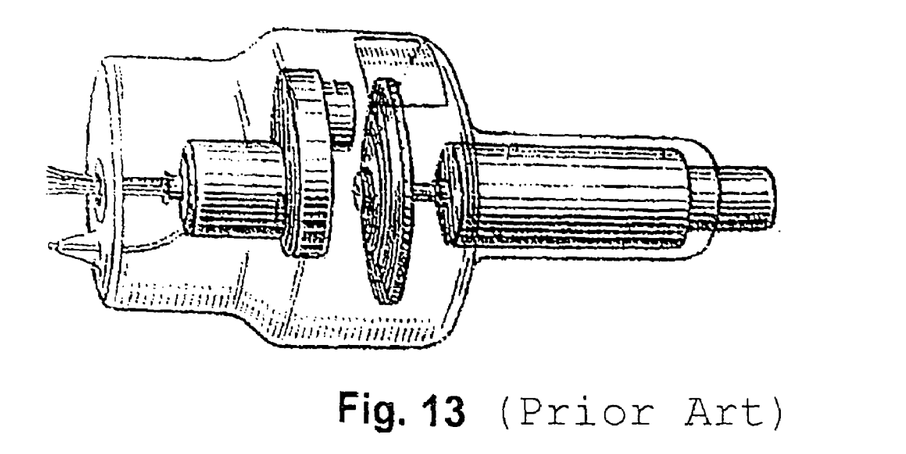
FIG. 13 illustrates a Prior Art device including an X-ray tube equipped with a rotating anode.

FIG. 10 depicts another "geometry", being characteristic to a greater extent for an X-ray source made as a tube (the position 1 depicts it conventionally) with a rotating anode. When such tube is used, the radiation source is linear. The tube has two output windows. The X-ray optical devices can "takes" only the radiation, emerging from these two windows. Several (5–10) monochromators 33 are placed at different angles on the path of the quasi-parallel beam 4, formed by the X-ray "half" lens 2, to provide a capability of working of plenty of the analytical devices. The said monochromators "intercept" different parts 34 of the cross-section of the initial beam 4, emerging from the "half" lens 2, and direct the reflected parts 35 of the said initial beam 4 to the analytical devices 5. Crystals with shear planes, being nonparallel to the crystal planes, and layer structures can be used as the monochromators 33. A type of a monochromator and its orientation angle relatively to the X-ray beam direction, emerging from the "half" lens, define the required degree of collimation of the part of the beam, diffracted on the said monochromator.

Thus, when an X-ray tube is used as a source of the divergent radiation, the channels of radiation transporting to the analytical devices can be divided in the following parts:

in the "geometry", shown in FIG. 1:

a space between the X-ray tube 1 (more exactly an anode of the said tube) and the input face of the X-ray lens 2 or 6 (in limits of the solid angle 3);

the channels of the X-ray lens 2 or 6;

a space between the output face of the X-ray lens 2 or 6 and the analytical device 5 or 8 (in limits of the cross-section of the output beam 4 of the lens 2 or the solid angle 7, corresponding to the output beam of the lens 6);

in the "geometry" shown in FIG. 10:

a space between the X-ray tube 1 (more exactly an anode of the said tube) and the input face of the X-ray lens 2 (in limits of the solid angle 3);

the channels of the X-ray lens 2;

a space between the output face of the X-ray lens 2 and the monochromator 33 (in limits of the cross-section of the part 34 of the output beam 4 of the lens 2);

a space between the monochromator 33 and the analytical device 5 (in limits of the cross-section of the beam 35, reflected by the monochromator).

Let's compare the parameters of a radiation of the modern synchrotrons and an X-ray tube, being a part of the complex of the suggested construction.

In the book [1] in FIG. 15 (p. 20) a radiation brightness curve of the English synchrotron "Doris" (E=2 GeV, the current is equal to 300 mA) is given. As one can see in this figure, at approximately 10 keV this synchrotron radiates $10^{10}$ foton/s eV (mrad)$^2$, i.e. in the narrow solid angle equal to 1 mrad and the narrow spectral range equal to 1 eV, "Doris" radiates of $10^{10}$ photons order per a second. An X-ray tube of 1 W power radiates isotropic approximately $3 \cdot 10^{11}$ photons per the same time. These photons are quasi-monochromatic photons in the spectral range of about 10 eV width. Correspondingly a tube of 10 kW power radiates $3 \cdot 10^{15}$ photons per a second.

The following quantity of photons, being transported quasi-parallel with the angular divergence of about 3 mrad, can be produced by means of the X-ray "half" lens, transforming a divergent radiation to a quasi-parallel one and being used in the suggested complex:

$$N = 3 \cdot 10^{15} \cdot \alpha \cdot \pi \cdot (\Delta\theta_3)^2 / 4\pi \text{ phot}/s \cdot (3 \text{ mrad})^2 \cdot 10 \text{ eV},$$

where $\Delta\theta_3$— is an aperture of the radiation capture of the X-ray tube by the "half" lens, α is a transmission coefficient of the "half" lens.

Considering that $\Delta\theta_3 = 0,1$ rad, $\alpha = 0,3$, we get $$N = 2,5 \cdot 10 \text{ phot}/c \cdot eV \cdot (\text{mrad})^2,$$

i.e. the X-ray tube of the suggested complex of a mean power of 10 kW, conjugated with the optics, gives the intensity, being 25 times larger than the synchrotron "Doris" gives, in the same spectral and angular range. It is obvious that it is possible to obtain the radiation density about 10 keV, being equal with the synchrotron "Doris", in the suggested complex at the tube power only of 400 W. Such and even more powerful tubes are widely used in the scientific researches, for instance, in diffractometry. So, Philips Company uses a tube of 2,5 kW power for diffractometry.

Nowadays, the tubes with a rotating anode of 30–100 kW power are produced and freely sold. The cost of the said tubes including a generator is about 100,000 USD, i.e. is about 3 orders lower than the cost of a synchrotron.

The efficiency and utility of the usage of the suggested solution are obvious from the given calculations.

INDUSTRIAL APPLICABILITY

The suggested complex in view of its relative simplicity and low cost in comparison with the traditional means is available for wide range of specialists and it makes possible to widen significantly the applications of X-ray researches, tests and measures, providing an acceptable brightness of the radiation in the input aperture of the analytical devices. One can suggest, that in future the said complex will enjoy wide applications in big and medium physical laboratories.

SOURCES

1. Synchrotron Radiation. Ed. by K. Kunts. Moscow, "Mir", 1981.
2. V. A. Arkadiev, A. I. Kolomiitsev, M. A Kumakhov, et al. Broadband X-ray optics with wide angular aperture. Uspekhi fizicheskikh nauk, 1989, volume 157, issue 3, pp. 529–537.
3. U.S. Pat. No. 5,192,869 (published Mar. 9, 1993).
4. V. A. Andreevsky, M. V. Gubarev, P. I. Zhidkin, M. A. Kumakhov, A. V. Noskin, I. Yu. Ponomarev, Kh. Z. Ustok. X-ray waveguide system with a variable cross-section of the sections. The IV-th All-Union conference on Interaction of Radiation with Solids. Book of Abstracts (May 15–19, 1990, Elbrus settlement, Kabardino-balkarian ASSR, USSR, pp. 177–178).
5. U.S. Pat. No. 5,570,408 (published Oct. 29, 1996).
6. R. Volsdet. Applied spectrometry of X-rays. Moscow, Atomizdat, 1977.
7. European application No. EP 0 742 150 (published Jul. 31, 1996).
8. U.S. Pat. No. 5,175,755 (published Dec. 29, 1992).
9. U.S. Pat. No. 5,497,008 (published Mar. 5, 1996).
10. European patent No. EP 0 555 376 (published Mar. 18, 1998).

What is claimed is:

1. A measuring and testing complex for carrying out researches in an X-ray range of radiation on multiple analytical stations simultaneously, each analytical station being configured for performing predetermined measurements or tests, the complex comprising:

a single non-synchrotron radiation source for producing X-rays in a form of a single divergent beam, multiple radiation transporting channels for transporting radiation from the single non-synchrotron radiation source to the respective multiple analytical stations, and multiple X-ray lenses corresponding to the multiple analytical stations, each of the X-ray lenses having a number of bent channels configured to provide multiple total external reflection of X-rays from walls of the bent channels, each of the X-ray lenses being configured to extract a part of the single divergent beam produced by the radiation source and transform the part the single divergent beam into a quasi-parallel beam, each of the radiation transporting channels being configured to include one of the X-ray lenses and to provide propagation of the extracted part of the single divergent beam and the quasi-parallel beam in an air medium to an input aperture of the corresponding analytical station.

2. The complex according to claim 1, wherein a distance between the analytical station and the corresponding X-ray lens being selected so as to provide a predetermined distance between quasi-parallel beams provided by different radiation transporting channels in an area adjacent the analytical station.

3. The complex according to claim 1, wherein the non-synchrotron radiation source includes an X-ray tube.

4. The complex according to claim 1, wherein the non-synchrotron radiation source includes a plasma X-ray source.

5. The complex according to claim 1, wherein the non-synchrotron radiation source includes a laser X-ray source.

6. The complex according to claim 1, wherein at least one of the analytical stations is configured for carrying out diffractometry researches and comprises:
    means for placing and orienting a sample under study with respect to the quasi-parallel beam, which is directed to the input aperture of the analytical station,
    a detector of radiation diffracted on the sample under study,
    means for positioning the detector and the sample under study relative to each other, and
    means for data processing and imaging responsive to an output of the detector.

7. The complex according to claim 1, wherein at least one of the analytical stations is configured for image formation of an internal structure of a sample and comprises:
    means for positioning the sample,
    a detector of radiation passed through the sample, and
    means for visualizing and registering an image.

8. The complex according to claim 1, wherein at least one of the analytical stations is configured for carrying out X-ray lithography and comprises:
    means for positioning a mask, and
    means for placing a substrate with a layer of resist applied on it,
    the means for placing is arranged behind the means for positioning the mask.

9. The complex according to claim 1, wherein at least one of the analytical stations is configured for carrying out spectrometric researches and comprises:
    a further X-ray lens having a number of bent channels configured to provide multiple total external reflection of X-rays from walls of the bent channels, the further X-ray lens is configured to provide radiation focusing of the quasi-parallel beam,
    means for positioning a sample under study in order to align a required portion of the sample with a region of X-rays focusing,
    a detector of radiation excited in the sample under study,
    a spectrometric channel coupled to an output of the detector, and
    means for data processing and imaging responsive to an output of the spectrometric channel.

10. A measuring and testing complex for carrying out researches in an X-ray range of radiation on multiple analytical stations simultaneously, each analytical station being configured for performing predetermined measurements or tests, the complex comprising:
    a single non-synchrotron radiation source for producing divergent X-rays,
    multiple radiation transporting channels for transporting radiation from the single non-synchrotron radiation source to the respective multiple analytical stations,
    an X-ray lens having a number of bent channels configured to provide multiple total external reflection of X-rays from walls of the bent channels,
    the X-ray lens being configured to extract a part of the divergent X-rays produced by the radiation source and transform the part the divergent X-rays into a quasi-parallel beam,
    multiple monochromators arranged so as to extract and reflect different parts of the quasi-parallel beam,
    the X-ray lens being common for the multiple radiation transporting channels configured to provide propagation of the extracted part of the divergent X rays and the quasi-parallel beam,
    the multiple radiation transporting channels being further configured to include said multiple monochromators and to provide propagation of the different parts of the quasi-parallel beam extracted and reflected by the monochromators in an air medium to input apertures of the respective analytical stations.

11. The complex according to claim 10, wherein the non-synchrotron radiation source includes an X-ray tube.

12. The complex according to claim 10, wherein at least one of the analytical stations is configured for carrying out diffractometry researches and comprises:
    means for placing and orienting a sample under study with respect to the quasi-parallel beam, which is directed to the input aperture of the analytical station,
    a detector of radiation diffracted on the sample under study,
    means for positioning the detector and the sample under study relative to each other, and
    means for data processing and imaging responsive to an output of the detector.

13. The complex according to claim 10, wherein at least one of the analytical stations is configured for image formation of an internal structure of a sample and comprises:
    means for positioning the sample,
    a detector of radiation passed through the sample, and
    means for visualizing and registering an image.

14. The complex according to claim 10, wherein at least one of the analytical stations is configured for carrying out X-ray lithography and comprises:
    means for positioning a mask, and
    means for placing a substrate with a layer of resist applied on it,
    the means for placing is arranged behind the means for positioning the mask.

15. The complex according to claim 10, wherein at least one of the analytical stations is configured for carrying out spectrometric researches and comprises:
    a further X-ray lens having a number of bent channels configured to provide multiple total external reflection of X-rays from walls of the bent channels, the further X-ray lens is configured to provide radiation focusing of the quasi-parallel beam,
    means for positioning a sample under study in order to align a required portion of the sample with a region of X-rays focusing,
    a detector of radiation excited in the sample under study,
    a spectrometric channel coupled to an output of the detector, and
    means for data processing and imaging responsive to an output of the spectrometric channel.

* * * * *